United States Patent [19]
Jaton et al.

[11] Patent Number: 5,712,377
[45] Date of Patent: Jan. 27, 1998

[54] GLYCOSIDES ISOLATED FROM POLLEN, THEIR SUGAR-FREE DECOMPOSITION PRODUCTS AND DERIVATIVES THEREOF

[75] Inventors: Jean-Claude Jaton, Thonex; Fabrizio Marazza, Novaggio; Ari Lewenstein, Zurich, all of Switzerland; Francis M. Sirotnak, New York, N.Y.; Bernhard Jaun, Fallanden, Switzerland

[73] Assignee: Cerbios-Pharma SA, Barbengo, Switzerland

[21] Appl. No.: 672,651

[22] Filed: Jun. 28, 1996

[30] Foreign Application Priority Data

Jun. 30, 1995 [CH] Switzerland ................. 1930/95

[51] Int. Cl.$^6$ .................... C07H 17/08; C07C 315/00
[52] U.S. Cl. .................... 536/7.1; 536/16.9; 536/17.4; 562/428
[58] Field of Search ................. 536/7.1, 16.9, 536/17.4; 562/428

[56] References Cited

FOREIGN PATENT DOCUMENTS 0220453   5/1987   European Pat. Off. .
3612278  10/1986   Germany .
9308799   5/1993   WIPO .

OTHER PUBLICATIONS

Lahiri et al., "Synthesis and Pharmacology of Some Pyrroles and Indan Amines: Hexahydro Indeno[1,2–c]Pyrroles and Indan Amines," *J. Pharmaceutical Sci.*, 57(6), 1013–1016 (Jun. 1988).

*Primary Examiner*—John Kight
*Assistant Examiner*—L. Eric Crane
*Attorney, Agent, or Firm*—Shenier & O'Connor

[57] ABSTRACT

What are described are new glucosides and their sugar-free decomposition products, as well as synthetically produced derivatives, which can be used as active components of pharmaceutical compositions. The novel glucosides have been isolated from aqueous extracts of vegetable pollen. These novel glucosides, sugar-free decomposition products and their derivatives have the effectiveness to modulate the immune system of warm blooded animals and they can be used as active components in pharmaceutical compositions for the treatment of tumors and virus-related diseases.

13 Claims, No Drawings

GLYCOSIDES ISOLATED FROM POLLEN, THEIR SUGAR-FREE DECOMPOSITION PRODUCTS AND DERIVATIVES THEREOF

CROSS-REFERENCE TO RELATED APPLICATIONS

This application claims the priority of Swiss Application No. 1930/95-4, filed on Jun. 30, 1995, the disclosure of which is incorporated herein by reference in its entirety.

BACKGROUND OF THE INVENTION

1. Field of the Invention

The present invention relates to novel glycosides, which are isolated from aqueous extracts of vegetable pollen and furthermore novel aglycones, which are obtained subsequently to the cleavage of the sugar moieties from said glycosides and derivatives of the novel aglycones. Said novel compounds can, for example be used as active components in pharmaceutical compositions.

2. Description of the Prior Art

Methods for the production of extracts from vegetable pollens have been known for a long time, and in this respect e.g. the German patent no. 1 467 750 and the Austrian patent no. 255 634 are to be mentioned, in which methods for the production of such pollen extracts are described, which are essentially devoid of the highly molecular proteins of the pollen envelope, which could possibly cause allergies. The corresponding pollen extracts and also mixtures thereof, obtained through aqueous extraction means, or by nonaqueous extraction means, are now for many years commercially available, and they are used as a tonic in order to increase the defense forces, for the treatment of prostate problems, for the acceleration of the recovering from lesions and bone fractures and as anti-inflammatory agents.

Furthermore the European patent no. 201 053 describes methods for the production of a pharmaceutical composition for the prophylactic treatment of allergies, containing as active component a corresponding pollen extract being obtained with aqueous extraction means or with nonaqueous extraction means.

Furthermore, it has also been tried to isolate fractions from pollen extracts obtained through aqueous extraction means and being devoid of highly molecular proteins, which are enriched with active components in the European patent no. 220 453 and the corresponding U.S. Pat. No. 4,952,399, the pollen extracts obtained through aqueous extraction means and being devoid of highly molecular proteins are used for the production of pharmaceutical compositions, which are blocking the growth of tumor cells. According to these patents, also those fractions of the pollen extract are used as active components that are enriched with amino acids and peptides and/or proteinaceous substances, or fractions displaying a molecular weight of less than 750, or in the range of 650–750, respectively.

The pollen extracts, which are described in said patents, or the fractions of the active components isolated from the pollen extracts display also a cytostatic activity, i.e. the growth of a variety of cancer cells, e.g. leukemia cells and human prostate cancer cells, throat cancer cells, liver cancer cells, bladder cancer cells and breast cancer cells, could be strongly blocked in corresponding cell cultures.

SUMMARY OF THE INVENTION

Further research, having been carried out with aqueous extracts of vegetable pollens, was leading now surprisingly to the isolation of protein fractions being free of active components, or active components being glycosides, or aglycones, which have been obtained through hydrolytic cleavage of the fractions of the glycosidic active components.

Surprisingly, it furthermore turned out that these fractions of the novel active components, or the aglycones obtained through their cleavage, are differing in their pharmaceutical activity with respect to the fractions of proteinaceous active components isolated previously from pollen.

The fractions of the novel active components, or the isolated active components obtained thereof, or the derivatives of synthetically produced novel active components are displaying the characteristic to modulate immune reaction of warm blooded animals.

DETAILED DESCRIPTION OF THE INVENTION

There have been novel glycosides being isolated from aqueous extracts of vegetable pollens having the following formula I

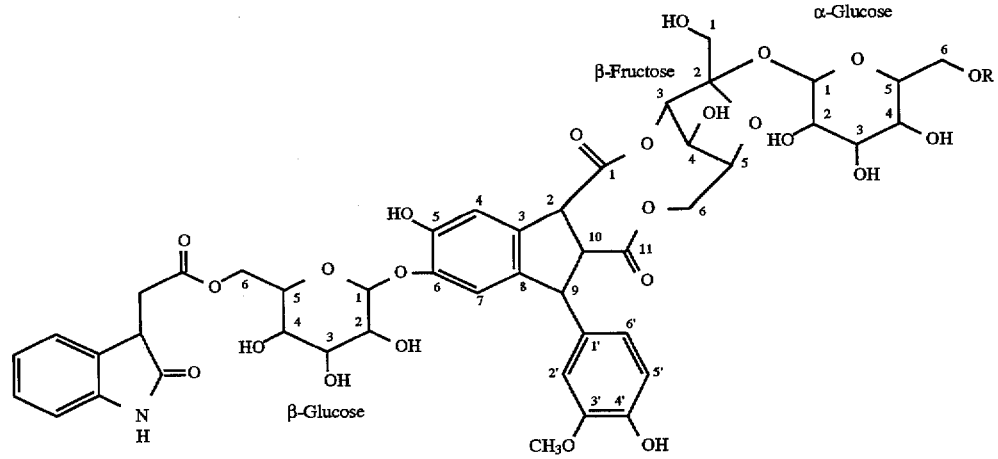

In this formula I R represents a hydrogen atom or a further sugar residue, particularly a glucose residue, being linked in a glycosidal linked to the above indicated glucose in the position 6.

Within the glycosides of the above indicated structural formula I, the residue of an unsubstituted 2-oxindole-3-acetic acid of the formula

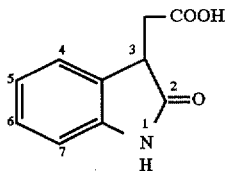
A is attached through its carboxylic group in an ester-like way to the hydroxy group in the position 6 of a molecule of glucose.

This glucose molecule has, on its turn, a β-glycosidic linkage to the phenolic hydroxy group of the position 6 of the indan system of an aglycone, having the following formula II

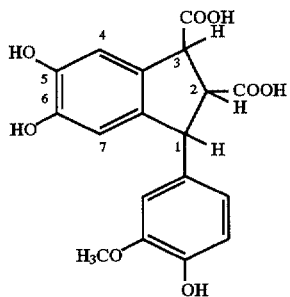
II

In this compound of the formula II there is also a phenyl ring, being substituted in the p-position by a hydroxy residue and in the m-position by a methoxy group, in the position 1 of the indan system. Furthermore the carboxy groups linked to the positions 2 and 3 within this compound according to formula II are in a cis-position next to each other, while the phenyl ring, being in position 1 of the indan system, is in a trans-position to the carboxy group which is linked in the position 2 of the indan system.

The indan derivative of the given formula II as well as the, here not indicated, possible sterical configuration relative to the position of the hydrogen atoms and the substituents in the positions 1, 2 and 3, are novel chemical compounds.

A further object of the present invention are therefore also these novel chemical compounds of the above indicated formula II and their different steroisomeric forms.

Within the glycoside of the formula I, both carboxylic acid groups of the dicarboxylic acid of the formula II are linked to the hydroxy groups in the positions 3 and 6 of the fructose residue in an ester-like way, i.e. under the formation of a 10-member dilactone ring.

In those glycosides of the formula I, in which R is a hydrogen atom, there is furthermore a residue of the α-glucose linked in a glycosidal linkage to the β-fructose, such that the bonded structure linked to both carboxylic groups of the compound according to formula II corresponds to two hexose units such as the one of saccharose.

In those compounds of the formula II, in which R represents a further hexose residue being linked in a glycosidal linkage, said hexose residue is preferably the residue of a further glucose unit.

From the indan compound of the formula II, further derivatives of the following formula III

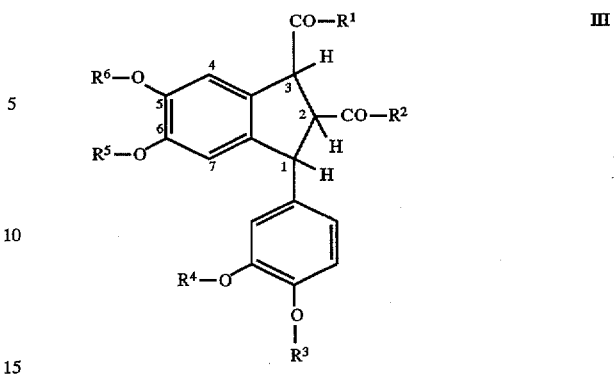
III could be obtained by synthesis.

In said derivatives $R^1$ and $R^2$ represent independently from each other, groups of the formula —O—X, wherein X stands for hydrogen, substituted or unsubstituted alkyl groups having 1 to 6 carbon atoms, e.g. aralkyl groups or substituted or unsubstituted aryl groups or one or more hexose residues bonded in an ester-like way or $R^1$ and $R^2$ represent both a bivalent group of the formula —O— or —O—Y—O—, whereby in these formulas Y stands for a bivalent organic residue, in particular an aliphatic, cycloaliphatic or aromatic hydrocarbon residue and $R^3$, $R^4$, $R^5$ and $R^6$ represent, independently from each other, hydrogen atoms, optionally substituted alkyl residues, optionally substituted cycloalkyl residues, optionally substituted aryl residues or acyl residues of aliphatic, cycloaliphatic or aromatic carboxylic acids or one or more hexose residues.

As already mentioned, the novel glycosides of the formula I were isolated from aqueous extracts of vegetable pollen of different species.

The starting material, from which the one fraction is isolated and which contains said glycosides, is an extract obtained by an aqueous extraction means from vegetable pollen, containing not more than 5 weight percent of high-molecular proteins or being free thereof. The production of these vegetable pollen extracts being devoid of high molecular proteins is carried out according to the method which is illustrated in claim 5 of the European patent no. 220 453.

While in the above mentioned European patent, precipitation procedures or column chromatographic separations were carried out in order to isolate from the mentioned pollen extracts a fraction enriched with amino acids, proteins and/or proteinaceous substances, in particular a fraction having a molecular weight of preferably in the range of 650–750, new different isolation procedures are performed in order to isolate such fractions being devoid of amino acids, proteins and/or proteinaceous substances and containing glycosides of the formula I.

A further object of the present invention is a method for the isolation of fractions containing glycosides from the pollen extract obtained by aqueous extraction means and this method is characterized in that the pollen extract, which can contain as further ingredient also maltodextrines, is dissolved in water and subjected to a dialysis with a membrane which is retaining substances of a molecular weight beyond 1000 Daltons, whereby the material which is diffusing through the membrane is discarded and in a second dialysis step the material which did not pass through the membrane is subjected to a dialysis by using a membrane which can retain materials having a molecular weight of over 3500 Daltons, preferably a membrane which can retain materials having a molecular weight of over 2000 Daltons, and then the dialysate passing through this membrane is evaporated under vacuum and fractions are isolated through gel filtration, containing the glycosides of the formula I.

According to an embodiment of this isolation method, the pollen extract, which is obtained in the form of a yellowish white powder, is dissolved in a 3 to 4 times amount of distilled water and this solution is dialyzed against water in the cold by using membranes raining substances having a molecular weight beyond 1000 Daltons. For example, said dialysis can be performed by using pipes of the molecular porous membrane, and it is advantageous to discard the material which has passed through said membrane after 24 hours and to use as an external solution a fresh solution of distilled water and to keep dialyzing for another 24 hours.

After said dialysis step, the inner solution, i.e. the material, which has not passed through the membrane, is concentrated, in general to a volume amounting to half of the volume of the aqueous solution, and is subjected to a dialysis.

This concentrated solution of the product being retained by the membrane is displaying a brown color and upon evaporation until the product is dry it turns out that the yield is amounting to 12 to 25%, based on the yellowish white powder which has been used as starting material.

In a second dialysis step the product obtained after lyophilization of the first dialysis step is dissolved in a 2 to 5 times amount of water and the aqueous solution is subjected to a dialysis against water by using a membrane retaining back products having a molecular weight of over 2000 Daltons. The dialysis is performed throughout a week, whereby the 20 times volume of water is being used as external solution and the external solution is changed daily.

The external solutions are united and concentrated and finally evaporated under vacuum until they are dry. The yield is amounting to 10 to 30%, based on the solid starting material which was subjected to this second dialysis step.

The material that has not passed through the membrane having an upper limit of 2000 Daltons after one week, i.e. the inner solution, is discarded.

The product obtained from this second dialysis shall be termed A2.

Three active fractions are isolated from this product A2 through gel filtration and shall be termed IIIa, IIIb and IIIc.

The fraction IIIb is separated in five fractions through a further, similarly performed gel filtration, whereby the fraction III-b5 is the one displaying the biggest activity in the pharmacological tests that have been performed.

This fraction III-b5 is further purified through high pressure liquid chromatography, whereby two major fractions are isolated, being termed III-b51 and III-b52, or abbreviated as b51 or b52.

It turned out that the fraction b51 and also the fraction D52 display a molecular weight of 1001 Daltons and that the mass spectra of b51 and b52 are virtually identical.

It furthermore turned out that b51 transforms into b52 in aqueous solution and vice versa, whereby subsequent to the transformation, no matter whether b51 or b52 is the starting point, the ratio is amounting to 60 weight percent of b51 and about 40 weight percent of b52.

Through further analytical examination by means of nuclear magnetic resonance spectra it could be furthermore shown that the glycoside b51 as well as the glycoside b52 are a compound of the formula I, wherein the residue R represents hydrogen.

Although this glycoside of the formula I displays a huge number of chiral centers, namely e.g. the carbon atoms in the positions 2, 10 and 9 of the indan system, the distinction, however, between the glycoside b51 and the glycoside b52 is caused only by the different configuration of the chiral center of the indolyl acetic acid. Corresponding investigations have shown that the glycoside b51 is distinguishing itself from glycoside b52 with regard to the configuration of the chiral center of the carbon atom in the 3 position of the 2-oxindol-3-acetic acid.

When the glycoside of the formula I, in which R represents a hydrogen atom, is hydrolyzed under strongly acidic conditions, then the 2-oxo-1,2,3,4-tetrahydroquinolin-4-carboxylic acid is formed from the 2-oxindol-3-acetic acid of the formula A and also the indan dicarboxylic acid of the formula II is separated from the sugar residues as aglycone.

The 2-oxindol-3-acetic acid of the formula A as well as the 2-oxo-1,2,3,4-tetrahydroquinolin-4-carboxylic acid are known for a long time in the form of their racemates. The indan derivative of the formula II represents, however, as already mentioned, a new chemical compound.

The indan derivative of the formula II displays a molecular weight of 360 Daltons, This dicarboxylic acid however is readily cleaving water due to the cis-position of both carboxylic groups, such that in the mass spectrum, depending on the recording conditions, virtually only a mass peak corresponding to an anhydride is observed, i.e. displaying an 18 Dalton inferior molecular weight, i.e. a molecular weight of 342 Daltons.

Furthermore, two main peaks can be isolated from the fraction IIIa through column chromatography, that are termed A3 and A4. From these, the peak A3 is yielding three major fractions being termed as A31, A32 and A34 obtained through high pressure liquid chromatography.

From the second peak termed A4 two fractions can be isolated through high pressure liquid chromatography and are termed A41 and A42. Each of both fractions displays a molecular weight of 1163 Daltons, and it turned out that in an aqueous solution, there is again an equilibrium between A41 and A42.

With acidic hydrolysis, the couple A41/A42 yields among others an aglycone being identical with said aglycone that has been obtained by acidic hydrolysis from the couple b51/b52.

Through further investigation, evidence can be found that the couple A41/A42 is the one glycoside of the formula I, in which R represents a further glucose residue having a glycosidic linkage to the glucose residue of the saccharose part.

If the couple A41 A42 is treated with an α-glucosidase, then the glucose residue R is cleaved from the compound of the formula I, and the couple b51-b52 is obtained, i.e. the one compound of the formula I, wherein R is a hydrogen atom.

In the same way, as illustrated above for the glycoside b51 and the glycoside b52, the glycoside A41 is distinguishing itself from the glycoside A42, only with regard to the configuration of the chiral center being formed through the carbon atom in the 3-position of the hetrocyclic ring of the residue of the 2-oxindol-3-acetic acid.

While, as already mentioned, the compound of the formula I, whereby R is a hydrogen atom and also the compound of the formula I, wherein R stands for the glycose residue being bonded in an α-glycosidic way provides through acidic hydrolysis, e.g. by using 1-normal hydrochloric acid at 100° C., the aglycone of the formula II and also the aglycone 2-oxo-1,2,3,4-tetrahydroquinolin-4-carboxylic acid formed from 2-oxindol-3-acetic acid of the formula A, it is only possible under mild basic conditions to cleave the 2-oxindol-acetic acid residue linked to the glucose residue, thus providing a new glycoside corresponding to the following formula IV pharmaceutical compositions, which allow the treatment of tumors, a variety of virus related diseases, in particular those which are caused through retro viruses, e.g. AIDS, and other syndromes which are related so to a weakening of the immune system, or to the reduced immune reaction, respectively.

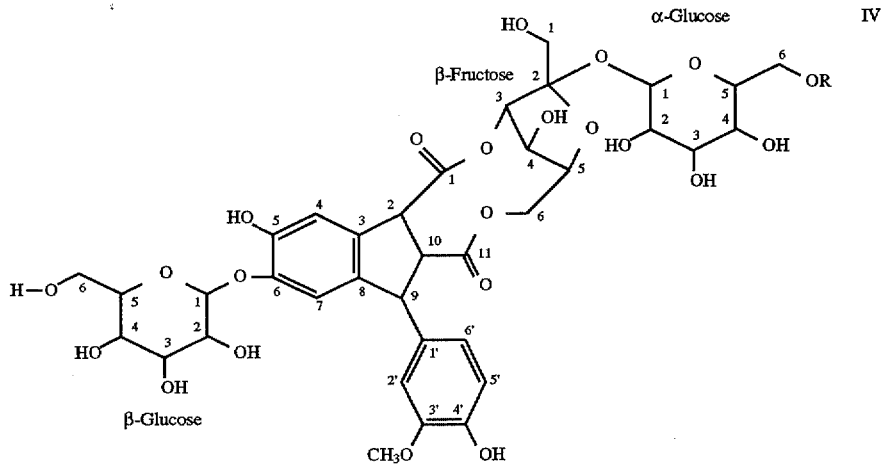

whereby in this formula, R represents a hydrogen atom or a hexose residue, being identical with the hexose residue of the starting material. In a corresponding way the residue R in the meaning of a hexose residue is preferably an α-glucosidically bonded glucose residue.

Through further treatment, glucose residues can be separated from this glycoside, e.g. a residue R in the meaning of a glucose residue being bonded in an α-glucosidal linkage through treatment with an α-glucosidase are separated, so that corresponding products of the above indicated formula are obtained, in which R represents hydrogen.

Furthermore, it is also possible in any desired order of succession to cleave the glucose residue being bonded to the phenolic OH-group and furthermore to cleave the residue of the β-glucose linked to both dicarboxylic acid residues in a ester-like way, so that eventually from the glycoside of the above indicated formula the aglycone of the above indicated formula II is obtained through stepwise cleavage of the sugar residues, or saccharose, respectively.

The novel glycosides of the formula I and the above indicated formula IV as well as the aglycone of the formula II and the derivatives of the formula III obtained thereof display interesting pharmacological activites. Thus, these novel compounds are, for example, capable to cause a modulation of the immune system of warm blooded animals.

A further object of the present invention are pharmaceutical compositions for the modulation of the immune system of warm blooded animals, which is characterized in that it comprises as an active component a glycoside of the above indicated formula I or IV or an aglycone of the above indicated formula II or a derivative of the aglycone of the above indicated formula III.

Further tests were showing that the effectiveness of the inventive novel glucosides, aglycones and derivatives thereof was blocked if there are furthermore such factors present at or leading to a blocking of the stimulation of the macrophase or to a blocking of the stimulation of the T-cells.

The novel glucosides of the formulae I and IV as well as the aglycone of the formula II and its derivatives of the formula IV, can be used as active components in such Through corresponding tests it could be shown that the life expectancy of mice, in which a variety of cancer cells were implanted, could be prolonged through the administration of the glucosides of the formulas I and IV and through the administration of the aglycone and its derivatives considerably and in comparison to a comparative group having not benefited from the administration of such novel compounds. Particularly good effects could be proved with implanted lung cancer (Lewis lung), sarcoma (S180) and breast cancer (E0771) and a certain activity with fibrosarcoma (T241) and large intestinal cancer (C38). Even cancer tumors of mice which have been forming after the implantation of corresponding cancer cells could be completely healed through the administration of these compounds.

Preferred embodiments of the method for the isolation of the new glucosides of the formula I from the aqueous extract of pollen are being described in the following examples.

However the following examples are not to be construed as being limiting to the entire scope of the present invention.

Furthermore also methods for the production of sugar-free decomposition products of these glucosides are illustrated.

EXAMPLE 1

Isolation of those fractions of pollen extracts being enriched with glucosides of the formula I.

From vegetable pollens, e.g. rye, an aqueous pollen extract is produced through extraction by means of a mixture of water and a completely water soluble organic solvent, e.g. acetone. For this purpose the pollen is stirred at a temperature of 30° to 32° C. for 48 hours, Thereby the high-molecular proteins and sugar of the pollen are decomposed through autofermentation. Stirring is maintained for another 20 to 30 hours at 30° C.

The aqueous medium was filtered from the pollen, and the clear solution thus obtained was evaporated under vacuum until it was dry. Thus, the dried vegetable pollen extract in the form of a yellowish-white powder was obtained.

Performance of the first dialysis step 80 g of the yellowish-white powder thus obtained were dissolved in 280 ml distilled water. This solution was filled in a pipe of a molecular porous membrane, which was letting substances having a molecular weight of less than 1000 Daltons pass through.

The length of the pipe was about 45 cm, and it was filled to about one-third of its total volume with this solution. Six of such pipes were produced and transferred into 10 liters of cold water and the dialysis was performed in the cold (around 4° C.) for 24 hours. After this time the external solution was removed, discarded and replaced with 10 l of cold water. After a further dialysis period of about 48 hours the material which remained in the pipes was removed and the content of each of the six pipes was evaporated under vacuum until it was dry.

Thus, about 20 g of a dry residue was obtained, corresponding to a yield of about 25% of the theoretical yield, based on the starting material.

Performance of the second dialysis step

This second dialysis step was performed by using a membrane that is retaining substances of a molecular weight of 2000 Daltons.

20 g of the dry product obtained from the first dialysis step were dissolved in 100 ml water, and the solution was filled in four dialysis pipes, each of them being filled up to one-third of its volume.

These four pipes were dialyzed against 2 l water during one entire day and then the external solution was removed and the dialysis was carried on with 2 l of fresh water. The dialysis was carried out for one week, whereas the external solution was changed every day.

Thereafter the external solutions were unified and at first concentrated to 100 ml and then evaporated completely until the product was dry.

After said week of dialysis, the remaining content of the pipe, i.e. the internal solution, was discarded.

Through this second dialysis step, about 5 to 6 g of a slightly yellowish colored powder was obtained, and the yield was amounting in a corresponding way to 25–30% of the theoretical yield, based on the material that was subjected to this second dialysis step.

Isolation of fractions from the product of the second dialysis step

The product of the second dialysis step was subjected to the gel filtration by using sephadex G-25 SF. Thus, a column having a diameter of 3.6 cm and a length of 90 cm was used. Deionized water was used as eluant and the flux of the eluant was amounting to 20 ml/hour. Fractions of 10 ml were captured.

Three fractions containing the active components were obtained and were termed IIIa, IIIb and IIIc.

The fraction IIIb was subjected to a further gel filtration by using a column filled with sephadex G-25 SF, and with the second gel filtration a total of five fractions were obtained, whereby the fraction III-b4 was. slightly yellowish and the fraction b5 contained 80% of the total solid, which were obtained through evaporation of each of the five fractions until they were dry.

The fraction III-b5 was subjected to a high pressure liquid chromatography, whereby two major fractions termed b51 and b52 were obtained. These fractions displayed an absorption of 280 nm in the UV-area, and they contained 40% of the solids, which were submitted to the high pressure liquid chromatography.

EXAMPLE 2

The same procedure as the one of example 1 was performed, whereby again said first dialysis step was carried out by using a membrane retaining substances of a molecular weight of at least 1000 Daltons, In this case 115 g of a yellowish white powder were dissolved in 500 ml of water and the dialysis was carried out against a volume of 10 l of water. The dialysis was performed during 48 hours in the cold, whereby the external solution was changed four times and was discarded.

The united internal solutions were lyophilized and 16 g of the dry product was thus obtained. The yield thereof was amounting to 14 weight percent based on the solid which was subjected to the dialysis.

The second dialysis step was performed by using a spectra pormembrane, retaining materials of a molecular weight of 3500 Daltons and more.

16 g of the product of the first dialysis step were dissolved in 40 ml water and dialyzed against 1 l of water for 24 hours, Then, the external solution was removed and stored, and it was again dialyzed for another 24 hours against 1 l of fresh water.

The dialysis was performed for a total of nine days while the external solution was changed daily, and after the ninth day the content of the pipes was discarded. The solid content of the external solution which was evaporated until it Was dry was as follows:

| External solution obtained after one day | Dry weight of the evaporation residue in mg |
| --- | --- |
| 1 | 600 |
| 2 | 500 |
| 3 | 250 |
| 4 + 5 | 400 |
| 6 + 7 | 200 |
| 8 + 9 | 200 |

A total of 2'150 mg were obtained after these nine-day dialysis, and these dry residues of the external solution were united and subjected to further gel filtrations.

2 g of the product of the second dialysis step were applied into a column which was filled with sephadex G-25 SF having a diameter of 2.6 cm and a length of 90 cm.

The conditions described in example 1 were maintained for this gel filtration and again three fractions were obtained, which displayed after evaporation, until they were dry, the following solid content:

IIIa: 45 mg

IIIb: 39 mg

IIIc: 22 mg.

The fraction III-b was separated into five fractions of the active components by using a column was which filled with sephadex G-25 SF, and were termed III-b1, b2, b3, b4 and b5. It turned out that the fraction b5 contained 80% of the solids of all fractions b1 to b5.

This fraction III-b5 was further purified by means of high pressure liquid chromatography, whereby two fractions were obtained, displaying a light absorption at 280 nm. These two fractions were termed b51 and b52.

EXAMPLE 3

Through structural investigation by means of infra-red spectrometry and nuclear magnetic resonance it could be shown that the fractions obtained according to example 1 and example 2 having the symbols b51 and b52, contained the one glucoside of the above mentioned formula I, wherein R is hydrogen and the molecular weight is 1001 Daltons.

It could be shown that a mixture of b51 and b52 was slowly forming from the pure fraction b51 in water and that, on the other hand, the pure fraction b52 in water was a mixture of b51 and b52 with the same ratio of the mixture. The equilibrium in the aqueous solution is at about 40 weight percent of b52 and 60 weight percent of b51. A fraction b51 and a fraction b52 can again be isolated by means of column chromatography.

Further investigations showed that the product b51 and the product b52 represent stereoisomeric forms with regard to the carbon atom in the position 3 of the heterocyclic ring of the molecular part of 2-oxindole-3-acetic acid.

EXAMPLE 4

According to example 1 and example 2 three fractions with the symbols IIIa, IIIb and IIIc were isolated through gel filtration on a column being filled with sephadex G-25.

In this example the fraction IIIa is subjected to a further separation by using a column being filled with sephadex G-25. 140 mg of the fraction IIIa were applied onto this column and by means of this gel filtration a fraction with the symbol A3 was obtained, which was delivering after evaporation about 30 mg of a solid and a further fraction with the symbol A4 was providing 66 mg after evaporation until it was dry.

The total quantity which was contained within the fractions A3 and A4 was corresponding to a yield of 65% of the applied solid.

The fraction A3 was subjected to a high pressure liquid chromatography and thereby two major fractions carrying the symbols A41 and A42 were obtained.

The active components of both fractions displayed a molecular weight of 1163 Daltons and the mass spectrum of the fraction A41 was identical with the one of fraction A42.

The mass spectrum of these fractions A41 and A42 was about 162 Daltons higher than the one of the fractions b51 and b52 obtained according to example 3, which allows the conclusion that the couple of active components b51/b52 isolated according to example 3 and the couple of active components A41/A42 which has been isolated now is distinguishing itself by a hexose unit being bonded in a glycosidal linkage.

Through further analytical investigations it could be moreover proven that the aglycone of the couple A41/A42 having been formed through acidic hydrolysis is identical with the aglycon of the couple b51/b52, and that through nuclear magnetic resonance spectra it could be proven that the couple of glucosides A41/A42 correspond to the formula I, whereby R is the residue of a glucose unit.

The glucosides within the glucoside couple A41/A42 are equally swapping in aqueous solution, whereby, no matter whether the starting point is the glucoside A41 or the glucoside A42, for some time an identical equilibrium mixture 1 is forming. Also in this case a difference between the glucoside A41 and the glucoside A42 is consisting in the stereo configuration with respect to the chiral center in the position 3 of the indole ring of the 2-oxindole-3-acetic acid.

EXAMPLE 5

The glucoside couple b51/b52 isolated according to example 2 was treated under mild basic conditions. Thereby, a glucoside of the following structure

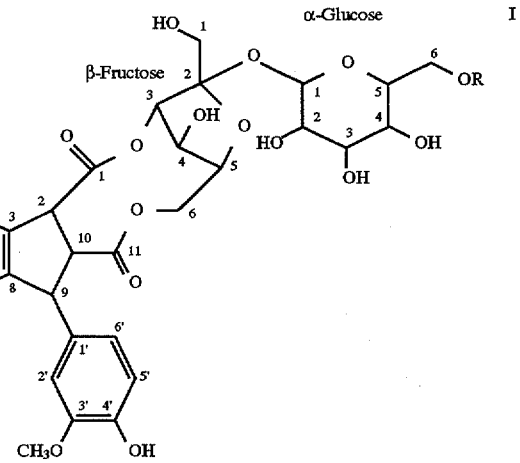

could be isolated, whereby in this glucoside R represents a hydrogen atom and Z represents equally a hydrogen atom.

EXAMPLE 6

In this example the glucoside couple A41/A42 obtained according to example 4 was subjected to a treatment with the β-glucosidase under alkaline conditions.

In this case a glucoside was obtained, which corresponds to the structure as indicated in example 5, whereby, however, the residue R was now a glucose residue being bonded in a glycosidal linkage.

EXAMPLE 7

3 to 5 mg of the glucoside couple b51/b52 isolated according to example 3 were dissolved in 250–330 μl of a 1.0 normal hydrochloric acid. The solution was treated at 100° C. for six hours under vacuum.

Thereafter it was dried, washed with water and centrifuged, whereby a dark brown precipitation was obtained. The precipitation was discarded, and the supernatant was purified through high pressure liquid chromatography. Through this purification procedure, the aglycone, which can be illustrated in its relative configuration for the following formula II

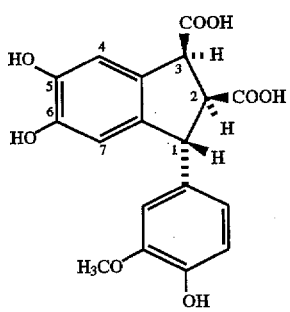

was isolated.

The structure of this Indan dicarboxylic acid was established through mass spectra and nuclear magnetic resonance spectra.

In the very same way, the glycosidic couple A41/A42 produced according to example 4, was subjected to acidic hydrolysis with 1-normal hydrochloric acid.

In this case too, the water soluble material was subjected to high pressure liquid chromatography and time compound having the above indicated formula II could again be isolated as aglycone.

EXAMPLE 8

Assay of the pharmacological effectiveness of glucosides of the formula I

Female mice being 5–7 weeks old and displaying a weight of 19–22 g were used in order to perform the pharmacological tests.

At the day 0, each animal was administered $1.5 \times 10^5$ tumor S180 cells through intraperitoneal injection.

At the day 1, the animals were classified in a random way into individual groups, whereby each group was comprising six mice and each group the animals were displaying a similar weight.

After one week, all animals of all groups had visibly been forming tumors.

In the group for comparison purposes (group i) the animals were not subjected to any further treatment. The glucoside of the formula I, in which R was a hydrogen atom, was administered through intraperitoneal injection to the animals of the groups 2–6. This glucoside was administered at day 1 in a dosage of 50 μg per mouse (group 2), or 75 μg per mouse (group 3), or 100 per mouse (group 4), or 150 μg per mouse (group 5), or μg 200 μg per mouse (group 6), respectively. The injections were repeated in the same dosage at the days 3, 5, 7 and 9.

It turned out that through the highest applied dosage in the group 6 no toxic effect could be found with the animals.

Ten to twelve days after the beginning of the assay all animals of the group of comparison (group 1) have died due to the tumors. Concerning those mice that have been treated with the glucoside, a recovery of 50% of the animals could be achieved. At the end of this assay these animals were living for more than 50 days in good health. Concerning the remaining animals of the groups 2 to 6 a considerable retreat of the tumors was observed.

The results of the assay were similar with a variety of other human tumor cells, as was described above for tumor S-180-cells. Also in this case a rapid recovery of the tumors could be achieved by means of the glucoside of the formula I.

Furthermore the glucoside was tested with respect to its tumor activity within cell cultures. It turned out that this glucoside did not display any cytotoxic properties to the tumor cells.

This completely surprising healing of the tumors through administration of the natural products isolated from pollen extracts can therefore be explained by a modulation of the immunoreaction of the living animals and not through the cytotoxic property of the glucosides isolated from natural products.

EXAMPLE 9

Similar tests, as described in example 8, were carried out with the glucoside of the formula I, in which R is a further glycosidically bonded glucose residue. In this case the same test results were very similar to those of example 8. A complete healing was observed in 30% of the animals of the first test group even at the lowest dosage of only 50 μm per mouse/injection.

We claim:

1. A compound having the structural formula C

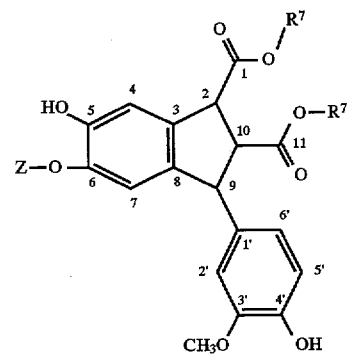

wherein

Z is selected from the group consisting of formula A

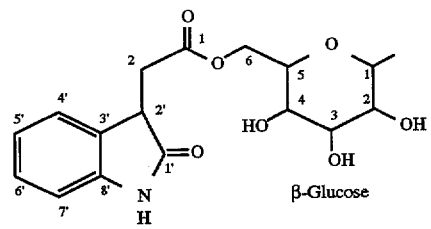

and formula B

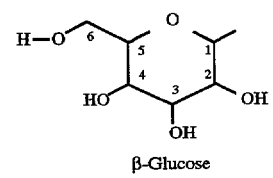

and each $R^7$ is a hydrogen atom or

Z is selected from the group consisting of a hydrogen atom, formula A, and formula B; and $R^7$ collectively have the formula D

15

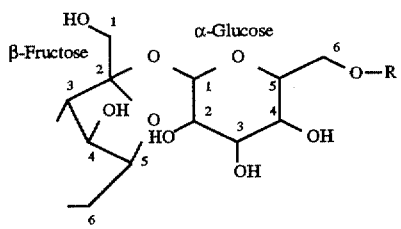

wherein
R is selected from the group consisting of a hydrogen atom, one or more hexose residues bonded in a glycosidal linkage, and two or more hexose residues.

2. Compound according to claim 1 having the structural formula I

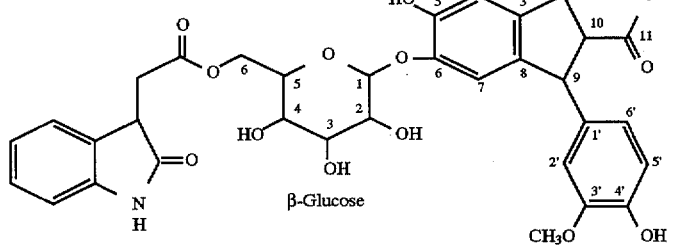

wherein
R is selected from the group consisting of a hydrogen atom, a hexose residue, and a glucose residue.

3. An indan derivative having the structural formula III

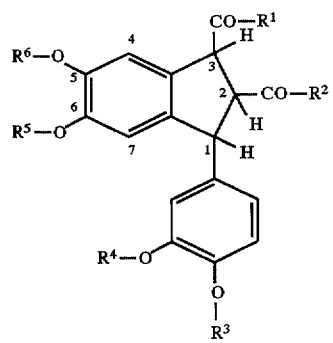     III wherein
$R^1$ and $R^2$ represent independently from each other the formula

—O—X wherein X is selected from the group consisting of
a) hydrogen,
b) a substituted or unsubstituted alkyl group having 1–6 carbon atoms,
c) an aralkyl group,
d) a substituted or unsubstituted aryl group, and
e) a hexose residue

16 or

D    $R^1$ and $R^2$ both represent a bivalent group of the formula

—O— or —O—Y—O wherein Y is a bivalent organic radical selected from the group consisting of
an aliphatic, a cycloaliphatic and an aromatic diradical
and
$R^3$, $R^4$, $R^5$, and $R^6$ are independently selected from the group consisting of:
i) a hydrogen atom,
ii) an alkyl residue,
iii) a cycloalkyl residue,
iv) an aryl residue,
v) an acyl residue of an aliphatic, a cycloaliphatic, or an aromatic carboxylic acid, and

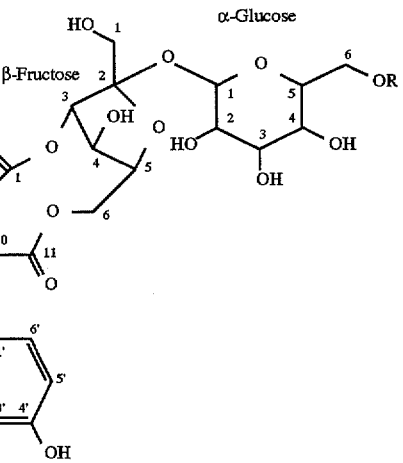     I vi) hexose residue.

4. Indan derivative according to claim 3, wherein $R^1$ and $R^2$ represent a hydroxyl group; $R^3$, $R^4$ and $R^5$ represent a hydrogen atom; and $R^6$ represents a methyl residue.

5. Indan derivative according to claim 3 having the structural formula IIIa

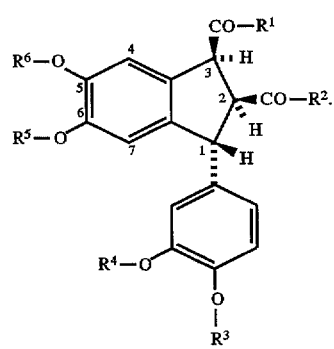     IIIa

6. Indan derivative according to claim 5, having the structural formula IIa

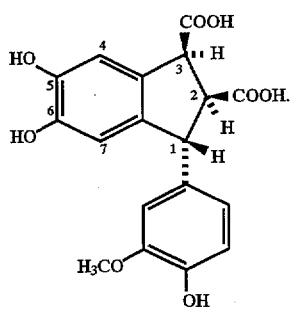

7. A method for the isolation of glycosides having the formula

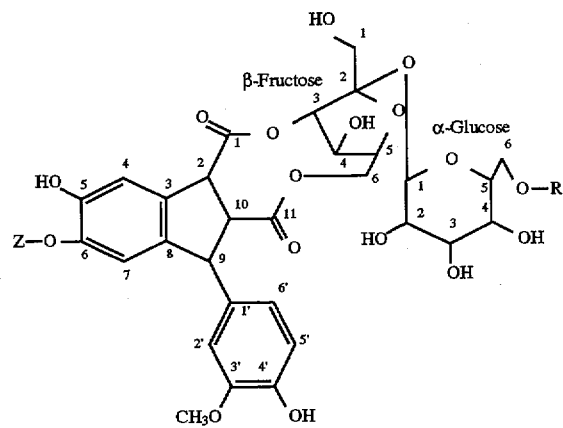

wherein the glycosides are derived from an aqueous extract of vegetable pollen and R is selected from the group consisting of a hydrogen atom and a hexose residue bonded by a glycosidal linkage and Z represents a glucosidal moiety of the formula A

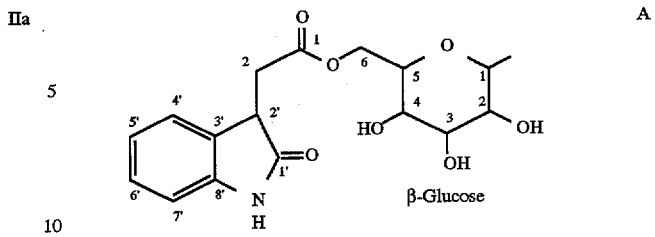

comprising the steps of: (i) subjecting the aqueous extract of vegetable pollen to dialysis by diffusing the extract through a first membrane which retains substances having a molecular weight greater than 1000 Daltons, (ii) diffusing the retained substances through a second membrane which passes substances having a molecular weight less than 3500 Daltons to obtain a dialysate, and (iii) isolating the glycosides from the dialysate by high-pressure liquid chromatography.

8. A process comprising the step of subjecting the isolated glycosides of claim 7 to an acid hydrolytic cleavage to produce an aglycone of the formula IIa

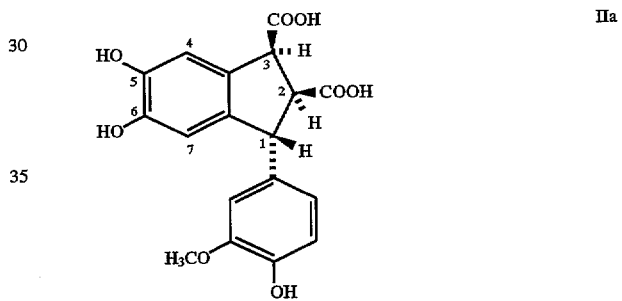

9. A process comprising the step of treating the isolated glycosides of claim 7 under slightly basic conditions, whereby glycosides having the formula

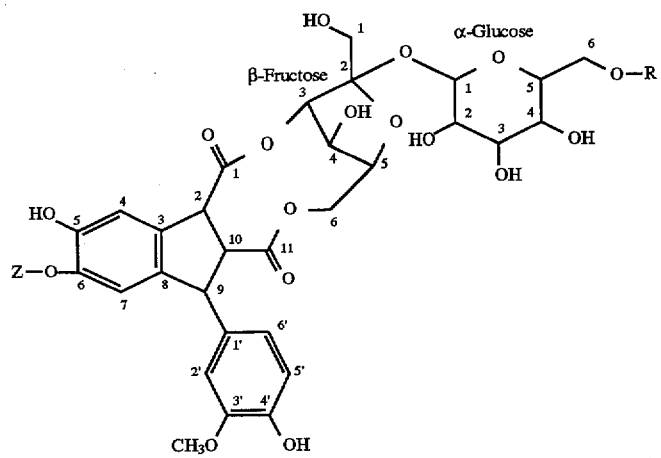

are obtained, in which Z represents the formula B

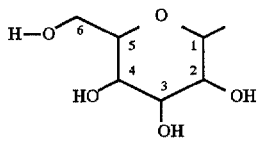

β-Glucose

10. A process comprising the step of subjecting the glycosides of claim 7 to ester cleavage whereby a glucoside of the formula

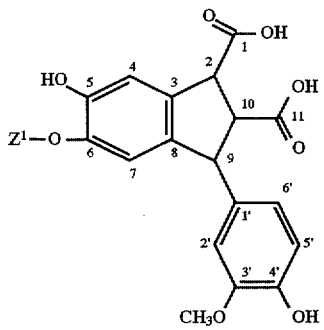

is isolated, in which $Z^1$ represents a glucosidal moiety of formula A

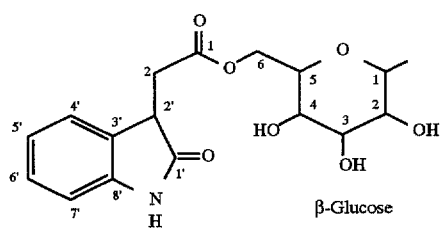

β-Glucose or a glucose residue of formula B

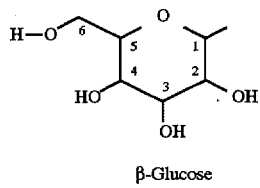

β-Glucose

11. A process for the production of an aglycone of the formula III

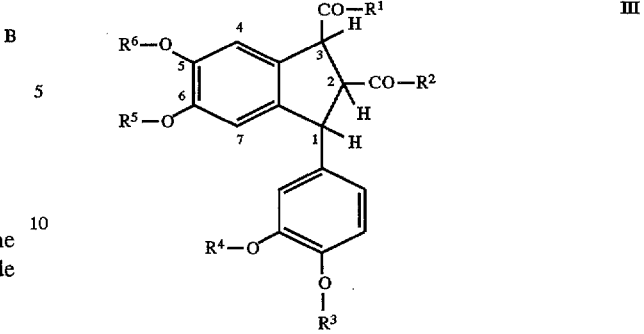

in which $R^1$ and $R^2$ represent hydroxy groups, $R^3$, $R^5$ and $R^6$ represent hydrogen and $R^4$ represents a methyl group, comprising the step of subjecting the isolated glycosides of claim 7 to an acid hydrolytic cleavage to produce said aglycone.

12. A process comprising the step of subjecting the aglycone of formula III of claim 11 to one of the reactions consisting of etherification, esterification, and ether cleavage to replace at least one of the hydroxy groups of $R^1$ and $R^2$, or to replace at least one of the hydrogen atoms of $R^3$, $R^5$, and $R^6$, or to replace the methyl group of $R^4$, respectively.

13. A process comprising the step of synthetically producing an aglycone having the formula IIIa

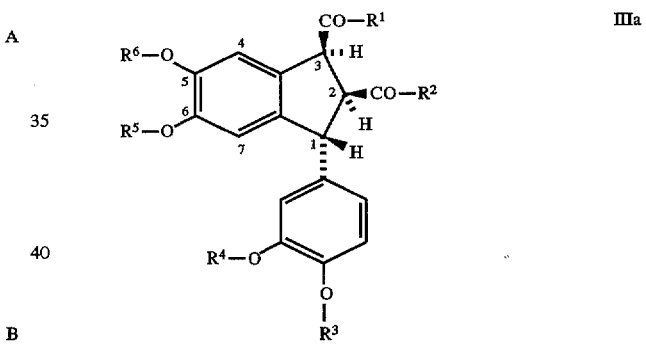

by subjecting the aglycone of formula III of claim 11 to one of the reactions consisting of etherification, esterification, and ether cleavage; to replace at least one of the hydrogen groups of $R^1$ and $R^2$, or to replace at least one of the hydrogen atoms of $R^3$, $R^5$, and $R^6$, or to replace the methyl group of $R^4$, respectively.

* * * * *